United States Patent [19]

Brown et al.

[11] 4,110,464
[45] Aug. 29, 1978

[54] INDOLOPYRONES HAVING ANTIALLERGIC ACTIVITY

[75] Inventors: Richard E. Brown, Hanover; Paul C. Unangst, Hackettstown, both of N.J.

[73] Assignee: Warner-Lambert Company, Morris Plains, N.J.

[21] Appl. No.: 772,036

[22] Filed: Feb. 25, 1977

Related U.S. Application Data

[62] Division of Ser. No. 611,453, Sep. 8, 1975, Pat. No. 4,028,383.

[51] Int. Cl.² ............................................. A61K 31/40
[52] U.S. Cl. .................................................... 424/274
[58] Field of Search ........................................ 424/274

[56] References Cited

U.S. PATENT DOCUMENTS 3,864,493   2/1975   Cairns et al. ...................... 424/283

OTHER PUBLICATIONS

Chemical Abstracts 80:59885x (1974).
Chemical Abstracts 79:105109b (1973).
Chemical Abstracts 79:115396g (1973).
Physicians Desk Reference (PDR) pp. 760–761 (1974).

*Primary Examiner*—Leonard Schenkman
*Attorney, Agent, or Firm*—Albert H. Graddis; Frank S. Chow; George M. Yahwak

[57] ABSTRACT

This invention relates to novel substituted indolopyrones which have utility in preventing allergic and asthmatic reactions in mammals.

6 Claims, No Drawings

INDOLOPYRONES HAVING ANTIALLERGIC ACTIVITY

This is a division of application Ser. No. 611,453 filed Sept. 8, 1975, now U.S. Pat. No. 4,028,383.

This invention relates to the substituted indolopyrones of the following general formula:

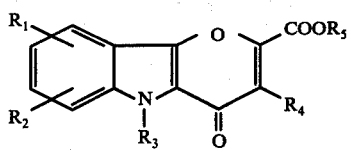

In this formula, $R_1$ and $R_2$ may be hydrogen, hydroxy, lower alkoxy or lower alkyl of 1 to 6 carbon atoms, halogen such as fluorine or chlorine, trifluoromethyl, or may be taken together to form a methylenedioxy group. $R_3$ may be hydrogen, lower alkyl of 1 to 6 carbon atoms, aryl or substituted aryl, such as phenyl, $R_4$ may be hydrogen, lower alkyl of 1 to 6 carbon atoms, or may be a halogen such as chlorine or fluorine and $R_5$ may be hydrogen or lower alkyl of 1 to 6 carbon atoms.

The compounds of this invention may be prepared by the following reaction sequence:

In the first step, an ester of a substituted indoxylic acid according to formula II is reacted with dimethylsulfone in the presence of a strong base to give a β-keto-sulfone according to structure III wherein $R_4$ is hydrogen.

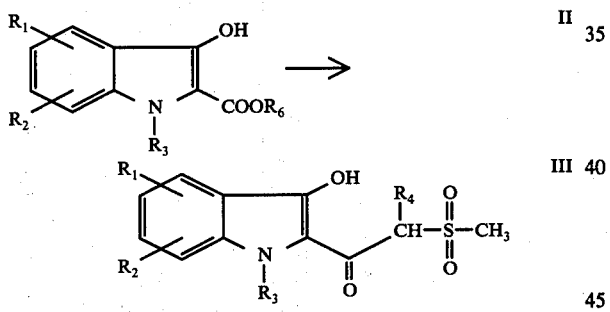

Among the bases which may be used are sodium hydride, sodium amide, potassium methoxide and the like. The reaction is conveniently carried out in a polar aprotic solvent as THF, DMF, DMSO and the like.

The starting materials according to structure II are known compounds and are prepared by methods described in the literature, or, if unknown, are easily prepared by the methods described in the literature for this class of compounds. In structures II and III, $R_1$, $R_2$ and $R_3$ are as described for I. $R_6$ is a lower alkyl group of 1 to 6 carbon atoms.

In the second step, the compound according to structure III wherein $R_4$ is hydrogen is treated with a lower alkyl halide or tosylate of 1 to 6 carbon atoms in the presence of a strong base and is thereby converted to a compound of structure III wherein $R_4$ is lower alkyl of 1 to 6 carbon atoms.

In the third step, the product according to structure III wherein $R_1$, $R_2$ and $R_3$ are as defined for structure I and $R_4$ may be hydrogen or lower alkyl of 1 to 6 carbon atoms is reductively cleaved to afford a compound of structure IV:

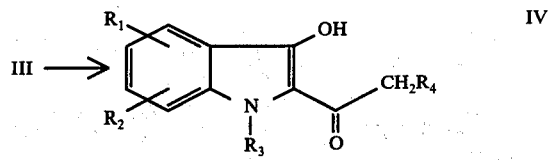

In structure IV, $R_1$, $R_2$, and $R_3$ are as defined for I and $R_4$ may be hydrogen or lower alkyl of 1 to 6 carbon atoms. This reductive cleavage is best carried out with aluminum amalgam or zinc dust in the presence of a lower alkyl organic acid such as acetic acid.

In the fourth step, the product of structure IV is reacted with a lower alkyl ester of oxalic acid in the presence of a strong base to give a product according to structure I in which $R_1$, $R_2$, $R_3$ and $R_4$ are as defined for structure IV and $R_5$ is a lower alkyl group of 1 to 6 carbon atoms. Among the strong bases which may be used for this reaction are sodium hydride, sodium amide, potassium t-butoxide, or, preferably, sodium ethoxide. The reaction is conveniently carried out in a solvent such as ethanol, THF, DMF, DMSO and the like.

In the final step, saponification of the ester of structure I wherein $R_5$ is a lower alkyl group of 1 to 6 carbon atoms is carried out to afford the acid of structure I, wherein $R_5$ is hydrogen.

In order to more fully disclose the compounds of the present invention, the following examples are given:

EXAMPLE 1

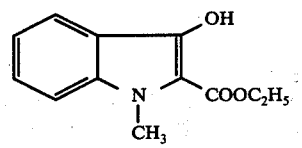

Ethyl-N-methylindoxylate

A mixture of 38.8g (0.2 mole) of ethyl chloromalonate and 44g (0.41 mole) of N-methylaniline was heated on the steam bath for 72 hours. After cooling, the mixture was diluted with 500ml of methylene chloride and unreacted N-methylaniline extracted with 4N HCl. The methylene chloride layer was dried and concentrated to 49g of oil. This was diluted with 49ml of hexamethylphosphoramide, and the mixture heated rapidly to boiling (bath temp. 245°). Reflux was continued for 20 minutes, the mixture cooled rapidly and poured into 400ml of 4N HCl. The crude solid product was filtered and recrystallized from isopropanol to give crytals, mp. 95°–96°.

EXAMPLE 2

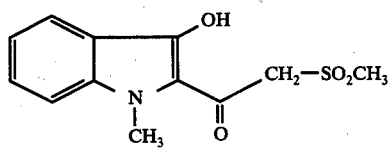

1-(3-hydroxy-1-methyl-1H-indol-2-yl)-2-(methylsulfonyl)ethanone

A solution of 56.4g (0.60 mole) dimethyl sulfone in 300ml dimethyl sulfoxide was added over 10 minutes to a nitrogen-filled flask containing 30.0g (0.62 mole) of sodium hydride (previously washed with pet ether). After stirring and heating at 65°-75° for 75 minutes, the mixture was cooled to room temperature, and 100ml of THF was added, followed by 43.8g (0.20 mole) ethyl N-methyl indoxylate in 250ml THF, added over 10 min. After heating an additional 2 hours at 65°-75°, the mixture was cooled and added to 2200ml of 0.55N ice cold HCl. After standing overnight, the product was filtered and recrystallized from methanol to give yellow needles, mpt. 168°-170°.

Anal. Calcd. for $C_{12}H_{13}NO_4S$: C, 53.92; H, 4.90; N, 5.24; S, 12.00. Found: C, 53.75; H, 4.99; N, 5.11; S, 12.04.

EXAMPLE 3

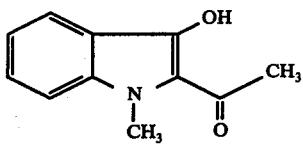

3-hydroxy-1-methyl-1H-indol-2-yl methyl ketone

A mixture of 17.0g (0.0637 mole) 1-(3-hydroxy-1-methyl-1H-indol-2yl)-2-(methylsulfonyl) ethanone, 21.0g (0.32 mole) zinc dust, 40ml glacial acetic acid and 80ml ab. ethanol was stirred vigorously and heated at 45°-50° for 1 hour. After stirring an additional hour at room temperature, the mixture was filtered through diatomaceous earth and the filter cake washed several times with fresh ethanol. The combined filtrates were condensed to 150ml and 50ml of hot water was added. Cooling yielded a green solid which was filtered, washed with cold water and recrystallized from 70% aqueous methanol to yield green needles of mpt. 119°-121°.

Anal. Calcd. for $C_{11}H_{11}NO_2$: C, 69.82; H, 5.86; N, 7.40. Found: C, 69.56; H, 5.85; N, 7.24.

EXAMPLE 4

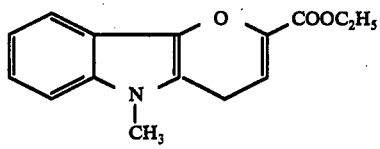

Ethyl 4,5-dihydro-5-methyl-4-oxopyrano[3,2-b]-indole-2-carboxylate

To a solution of 6.0g (0.26 mole) of sodium metal in 600ml ab. ethanol was added 18.0g (0.095 mole) of 3-hydroxy-1-methyl-1H-indol-2-yl methyl ketone, followed by 37.6g (0.26 mole) of diethyl oxalate, added over 10 min. The mixture was stirred and heated at reflux for 17 hours, cooled and the red di-sodium salt was filtered and washed with cold hexane. The crude salt was added to a solution of 28ml conc. HCl and 120ml ab. ethanol, heated at reflux for 30 min., and the mixture was filtered while hot. Cooling the filtrate gave the crude product, which was filtered and then dissolved in 400ml of chloroform. The chloroform solution was washed 3 times with dilute aqueous $NaHCO_3$, 1 time with water, dried ($MgSO_4$) and evaporated to leave a grey residue. Recrystallization from 15% $CHCl_3$ in hexane gave yellow needles of mpt. 160°-162°.

Anal. Calcd. for $C_{15}H_{13}NO_4$: C, 66.41; H, 4.83; N, 5.16. Found: C, 66.59; H, 4.81; N, 4.94.

EXAMPLE 5

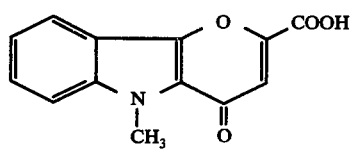

4,5-dihydro-5-methyl-4-oxopyrano[3,2-b]indole-2-carboxylic acid

A mixture of 5.40g (0.020 mole) of ethyl 4,5-dihydro-5-methyl-4-oxopyrano[3,2-b]indole-2-carboxylate in 80ml of 1% aqueous sodium hydroxide was stirred at room temperature for 30 min. The nearly one-phase mixture was extracted twice with 50ml $CH_2Cl_2$ and the aqueous layer was cooled in ice and acidified with 4N HCl. The gelatinous yellow crude product was filtered, digested for a few minutes on a steam bath with 100ml hot water and then re-filtered. Recrystallization from ab. EtOH gave yellow needles of mpt. 280°-dec.

Anal. Calcd. for $C_{13}H_9NO_4$: C, 64.20; H, 3.73; N, 5.76. Found: C, 64.02; H, 3.77; N, 5.94.

The compounds of this invention are useful in the prevention of allergic and asthmatic reactions in mammals. For example, in tests conducted by the procedures of I. Mota, Life Sciences, 7: 465 (1963) and Z. Ovary et al., Proc. Soc. Exptl. Biol. Med., 81: 584 (1952), these compounds are capable of protecting rats from allergic and asthmatic reactions at a dose level of 0.1 to 5 mg/kg when administered parenterally and at a dose level of 0.1 to 1.0 mg/kg when administered intravenously.

A passive cutaneous anaphylaxis procedure (see Brocklehurst, Handbook of Experimental Immunology, Blackwell Scientific Publishing Co., Oxford) also showed these compounds to be antiallergic. In this procedure, male rats, between 180 and 200 grams in weight are passively sensitized 48 or 72 hours prior to test with rat sera containing reagin-type antibodies. These sera are injected intradermally in four separate sites, two on each side of the ventral midline. Dose volume is 0.1 ml.

On the test-day animals receive drug or vehicle (placebo) 30 minutes prior to challenge. Test compounds are given i.p. on an mg/kg basis; usual volume is 0.5 ml/100 g body weight. Controls receive the vehicle, on the same weight-volume basis.

The challenging dose of 1.0 ml of Antigen-Evans Blue is administered i.v. This is prepared from either Ovalbumin or dinitrophenylated bovine gamma globulin, 10 mg, together with 5 ml of 0.5% Evans Blue, U.S.P., and 5 ml of normal saline. At 30 minutes after challenge each rat is sacrificed. A section of skin that includes the four sensitizing injection sites is removed.

Reaction is indicated by a blue coloration of the site and scored on the basis of color intensity. Size of the site is also reported.

| Score | Definition | Interpretation | Conclusion for Drug Activity |
|---|---|---|---|
| 0 | colorless | no PCA reaction | marked antagonism; activity |
| 1 | faint coloration | very slight reaction | moderate activity |
| 2 | light blue | partial reaction | very slight activity |
| 3 | dark blue | complete reaction | no activity |
| 4 | dark blue diffuse | over reaction | enhancement of infusion or serum is too strong |

Data is reported as the arithmetic mean score of a specific site for that group of five animals; the size of the spot is also reported as the mean for the group.

The relation between dilution of antibody and mean spot diameters approximates a straight line which is constructed by the method of least squares for the control animals. The maximum antibody concentration is set as "100% reactivity", with the extrapolated "zero" antibody concentration being 0%. Using this line the diameter at the highest antibody concentrations in any treated group is expressed as a percent of the control, i.e. "% inhibition." The treatment is judged "active" if the inhibition is 50% or greater. If the diameter of the treated group significantly differed from control statistically, but is less that 50% inhibition, the treatment is judged "slightly active".

Following this protocol, the results for the compound of Example 5 are tabulated below:

| Dose | Route | % Inhibition |
|---|---|---|
| 1.0 mg/kg | I.P. | 30 |
| 5.0 | I.P. | 100 |
| 10.0 | I.P. | 100 |
| 25.0 | I.P. | 100 |

As can be seen, this compound is highly effective as an antiallergic.

Having thus described our invention and the manner and process of making and using it in such full, clear, concise, and exact terms as to enable any person skilled in the art to which it pertains, or with which it is most nearly connected, to make and use the same, and having set forth the best modes for carrying out our invention;

We claim:

1. A method for the prevention of allergic and asthmatic reactions in mammals which comprises parenterally administering to said mammals an effective amount sufficient to prevent allergic and asthmatic reactions in mammals of a compound of the formula:

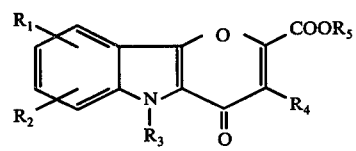

wherein $R_1$ and $R_2$ may be hydrogen, hydroxy, lower alkoxy or lower alkyl of 1 to 6 carbon atoms, halogen, trifluoromethyl, or taken together to form a methylenedioxy group; $R_3$ may be hydrogen, lower alkyl of 1 to 6 carbon atoms or phenyl; $R_4$ may be hydrogen, lower alkyl of 1 to 6 carbon atoms or halogen; and $R_5$ may be hydrogen or lower alkyl of 1 to 6 carbon atoms.

2. The method according to claim 1 wherein $R_1$, $R_2$, $R_3$, $R_4$, and $R_5$ may be hydrogen, or a lower alkyl.

3. The method according to claim 1 wherein $R_1$ and $R_2$ are hydrogen.

4. The method according to claim 1 wherein $R_3$ is a lower alkyl and $R_4$ is hydrogen.

5. The method according to claim 1 wherein $R_5$ is $C_2H_5$ and the compound is ethyl 4,5-dihydro-5-methyl-4-oxypyrano[3,2-b]-indole-2-carboxylate.

6. The method according to claim 1 wherein $R_5$ is hydrogen and the compound is 4,5-dihydro-5-methyl-4-oxopyrano[3,2-b]indole-2-carboxylic acid.

* * * * *